(12) United States Patent
Gass et al.

(10) Patent No.: US 11,361,863 B2
(45) Date of Patent: Jun. 14, 2022

(54) LOCATION-BASED WIRELESS DIABETES MANAGEMENT SYSTEMS, METHODS AND APPARATUS

(71) Applicant: ASCENSIA DIABETES CARE HOLDINGS AG, Basel (CH)

(72) Inventors: Jennifer L. Gass, Tarrytown, NY (US); Michael Harboun, Chicago, IL (US); Simon King, Chicago, IL (US)

(73) Assignee: Ascensia Diabetes Care Holdings AG, Basel (CH)

( * ) Notice: Subject to any disclaimer, the term of this patent is extended or adjusted under 35 U.S.C. 154(b) by 272 days.

(21) Appl. No.: 15/570,117

(22) PCT Filed: Apr. 29, 2016

(86) PCT No.: PCT/EP2016/059616
§ 371 (c)(1),
(2) Date: Oct. 27, 2017

(87) PCT Pub. No.: WO2016/174206
PCT Pub. Date: Nov. 3, 2016

(65) Prior Publication Data
US 2018/0137937 A1      May 17, 2018

Related U.S. Application Data (60) Provisional application No. 62/154,600, filed on Apr. 29, 2015.

(51) Int. Cl.
*G16H 40/67* (2018.01)
*G16H 20/10* (2018.01)
(Continued)

(52) U.S. Cl.
CPC .......... *G16H 40/67* (2018.01); *A61B 5/0022* (2013.01); *G06Q 10/06* (2013.01); *G06Q 10/109* (2013.01);
(Continued)

(58) Field of Classification Search
CPC ........ G16H 40/40; G16H 40/60; G16H 20/10; G06Q 10/06; G06Q 10/109; A61B 5/0022; A61B 5/14532; A61B 2560/0266
See application file for complete search history.

(56) References Cited

U.S. PATENT DOCUMENTS

| 5,575,403 A | 11/1996 | Charlton et al. |
| 6,540,672 B1 | 4/2003 | Simonsen |

(Continued)

FOREIGN PATENT DOCUMENTS

| CN | 1348558 A | 5/2002 |
| CN | 1921529 A | 2/2007 |

(Continued)

OTHER PUBLICATIONS

Taiwan Search report of related Taiwan Application No. 104123600 dated Jan. 24, 2019.
(Continued)

*Primary Examiner* — Devin B Henson
(74) *Attorney, Agent, or Firm* — Dugan & Dugan, PC (57) ABSTRACT

Embodiments provide systems, methods and apparatus for diabetes management using location-based reminders. Embodiments include requesting a user select a diabetes management related task to be reminded to perform; requesting the user select a location at which the user is to be reminded to perform the selected diabetes management related task; monitoring the user's location; detecting the user has entered the selected location; triggering the reminder in response to detecting the user has entered the
(Continued)

selected location; and presenting the reminder to the user. Numerous other aspects are provided like helping a user locate a blood glucose meter (BGM) by identifying a most recent data transfer from the BGM based on a stored date and time associated with the most recent data transfer from the BGM, and identifying patterns of diabetes management events corresponding to particular location types.

7 Claims, 9 Drawing Sheets

(51) Int. Cl.
*G16H 40/40* (2018.01)
*G16H 40/60* (2018.01)
*A61B 5/00* (2006.01)
*A61B 5/145* (2006.01)
*G06Q 10/06* (2012.01)
*G06Q 10/10* (2012.01)
*G16H 10/40* (2018.01)

(52) U.S. Cl.
CPC .............. *G16H 10/40* (2018.01); *G16H 20/10* (2018.01); *G16H 40/40* (2018.01); *G16H 40/60* (2018.01); *A61B 5/14532* (2013.01); *A61B 2560/0266* (2013.01)

(56) References Cited

U.S. PATENT DOCUMENTS

| | | | |
|---|---|---|---|
| 6,569,094 B2 | 5/2003 | Suzuki et al. | |
| 6,604,050 B2 | 8/2003 | Trippel et al. | |
| 6,607,484 B2 | 8/2003 | Suzuki et al. | |
| 6,674,821 B1 | 1/2004 | Mejyr | |
| 6,790,178 B1 | 9/2004 | Mault et al. | |
| 6,802,812 B1 | 10/2004 | Walker | |
| 6,819,013 B2 | 11/2004 | Kelly et al. | |
| 6,870,475 B2 | 3/2005 | Fitch et al. | |
| 7,039,420 B2* | 5/2006 | Koskinen ............ G06Q 10/109 |
| | | | 455/456.1 |
| 7,286,894 B1 | 10/2007 | Grant et al. | |
| 7,316,648 B2 | 1/2008 | Kelly et al. | |
| 7,394,405 B2* | 7/2008 | Godden ................... G08G 3/02 |
| | | | 340/988 |
| 7,549,961 B1 | 6/2009 | Hwang | |
| 7,779,183 B2 | 8/2010 | Koehler et al. | |
| 8,131,564 B2 | 3/2012 | Dicks | |
| 8,208,973 B2 | 6/2012 | Mehta | |
| 8,483,974 B2 | 7/2013 | Connolly | |
| 8,579,813 B2 | 11/2013 | Causey et al. | |
| 8,682,598 B2 | 3/2014 | Connolly et al. | |
| 8,755,053 B2 | 6/2014 | Fright | |
| 8,758,245 B2 | 6/2014 | Ray et al. | |
| 8,895,316 B2 | 11/2014 | Batman et al. | |
| 8,954,007 B2 | 2/2015 | Hillyard | |
| 9,179,844 B2 | 11/2015 | Fright | |
| 9,462,623 B2 | 10/2016 | Jakusovszky | |
| 9,696,980 B2 | 7/2017 | Dicks | |
| 9,750,896 B2 | 9/2017 | Kamen | |
| 9,861,285 B2 | 1/2018 | Fright | |
| 9,980,671 B2* | 5/2018 | Refvik ................... A61B 5/157 |
| 2001/0038343 A1 | 11/2001 | Meyer et al. | |
| 2005/0108057 A1 | 5/2005 | Cohen | |
| 2006/0009697 A1 | 1/2006 | Banet et al. | |
| 2006/0106433 A1 | 5/2006 | Mazar et al. | |
| 2006/0273930 A1 | 12/2006 | Godden | |
| 2007/0003061 A1 | 1/2007 | Jung et al. | |
| 2007/0027388 A1 | 2/2007 | Chou | |
| 2007/0171088 A1 | 7/2007 | Sato | |
| 2007/0181425 A1 | 8/2007 | Kim | |
| 2007/0254709 A1 | 11/2007 | Higgins | |
| 2007/0293910 A1 | 12/2007 | Strother et al. | |
| 2007/0299480 A1 | 12/2007 | Hill | |
| 2008/0092638 A1 | 4/2008 | Brennenman et al. | |
| 2008/0109302 A1 | 5/2008 | Salokannel et al. | |
| 2008/0300919 A1* | 12/2008 | Charlton ............ G06F 13/4081 |
| | | | 705/2 |
| 2009/0069642 A1 | 3/2009 | Gao et al. | |
| 2009/0116479 A1 | 5/2009 | Choi | |
| 2009/0163793 A1 | 6/2009 | Koehler | |
| 2009/0198141 A1 | 8/2009 | Hollinger et al. | |
| 2009/0213213 A1 | 8/2009 | Fright | |
| 2009/0243791 A1 | 10/2009 | Partin | |
| 2010/0000862 A1 | 1/2010 | Rao | |
| 2010/0111066 A1 | 5/2010 | Mehta | |
| 2010/0113897 A1 | 5/2010 | Brennenman et al. | |
| 2010/0165795 A1 | 7/2010 | Elder | |
| 2010/0228111 A1 | 9/2010 | Friman | |
| 2010/0331645 A1 | 12/2010 | Simpson | |
| 2011/0066044 A1 | 3/2011 | Moon | |
| 2011/0082711 A1* | 4/2011 | Poeze ................ A61B 5/14532 |
| | | | 705/3 |
| 2011/0117841 A1 | 5/2011 | Thorn | |
| 2011/0124996 A1* | 5/2011 | Reinke .............. A61M 5/14248 |
| | | | 600/365 |
| 2011/0165865 A1 | 7/2011 | Gao et al. | |
| 2011/0179405 A1 | 7/2011 | Dicks | |
| 2011/0256024 A1 | 10/2011 | Cole et al. | |
| 2011/0289497 A1 | 11/2011 | Kiaie | |
| 2011/0319813 A1 | 12/2011 | Kamen | |
| 2012/0019379 A1 | 1/2012 | Ben Ayed | |
| 2012/0123227 A1 | 5/2012 | Sun et al. | |
| 2012/0149245 A1 | 6/2012 | Ralston et al. | |
| 2012/0150556 A1 | 6/2012 | Galasso | |
| 2012/0190299 A1 | 7/2012 | Takatsuka et al. | |
| 2012/0238851 A1 | 9/2012 | Kamen | |
| 2012/0303638 A1* | 11/2012 | Bousamra ........... G06F 19/3475 |
| | | | 707/751 |
| 2013/0151266 A1 | 6/2013 | Randall | |
| 2013/0190674 A1 | 7/2013 | Case | |
| 2014/0012117 A1* | 1/2014 | Mensinger .............. A61B 5/742 |
| | | | 600/365 |
| 2014/0039840 A1* | 2/2014 | Yuen .................... A61B 5/0022 |
| | | | 702/189 |
| 2014/0149742 A1 | 5/2014 | Yau | |
| 2014/0266607 A1 | 9/2014 | Olodort | |
| 2014/0324445 A1 | 10/2014 | Carlsgaard | |
| 2014/0364056 A1 | 12/2014 | Belk | |
| 2014/0380218 A1 | 12/2014 | Refvik | |
| 2015/0123810 A1 | 5/2015 | Hernandez-Rosas | |
| 2015/0189461 A1 | 7/2015 | Pang et al. | |
| 2016/0337448 A1 | 11/2016 | Gofman et al. | |
| 2017/0030889 A1 | 2/2017 | Yao et al. | |
| 2017/0038847 A1 | 2/2017 | Schorsch | |
| 2017/0201931 A1 | 7/2017 | Swanzey et al. | |
| 2017/0208425 A1 | 7/2017 | Fu et al. | |
| 2017/0214780 A1 | 7/2017 | Gofman et al. | |
| 2017/0344718 A1 | 11/2017 | Chen | |

FOREIGN PATENT DOCUMENTS

| | | |
|---|---|---|
| CN | 101461969 A | 6/2009 |
| CN | 101675900 A | 3/2010 |
| CN | 201491011 U | 5/2010 |
| CN | 202075262 U | 12/2011 |
| CN | 102422657 | 4/2012 |
| CN | 102565413 A | 7/2012 |
| CN | 202838653 U | 3/2013 |
| CN | 101431456 | 7/2014 |
| CN | 205006870 U | 2/2016 |
| EP | 2352305 | 8/2011 |
| EP | 2741 528 A1 | 6/2014 |
| EP | 2887753 | 6/2015 |
| JP | H10-116460 | 5/1998 |
| JP | H10-170335 | 6/1998 |
| JP | 2003-173375 | 6/2003 |
| JP | 2003-216740 | 7/2003 |
| JP | 2004-154315 | 6/2004 |
| JP | 2007-111514 | 5/2007 |
| JP | 2007-228554 | 9/2007 |
| JP | 2007-243977 | 9/2007 |

(56) References Cited

FOREIGN PATENT DOCUMENTS

| | | |
|---|---|---|
| JP | 2008-186050 | 8/2008 |
| JP | 2010-124286 | 6/2010 |
| JP | 2011-019161 | 1/2011 |
| JP | 2011-511335 | 4/2011 |
| JP | 2012-157006 | 8/2012 |
| JP | 2012-230521 | 11/2012 |
| JP | 2013-201516 A | 10/2013 |
| JP | 2014-038432 | 2/2014 |
| JP | 2014-068076 | 4/2014 |
| JP | 2014-164348 | 9/2014 |
| TW | 201322167 A | 6/2013 |
| WO | WO0152727 | 7/2001 |
| WO | WO 2008/153825 | 12/2008 |
| WO | WO 2009/006486 | 1/2009 |
| WO | WO2009/074887 | 6/2009 |
| WO | WO20110609232 A2 | 5/2011 |
| WO | WO 2012/128485 | 9/2012 |
| WO | WO2013009771 | 1/2013 |
| WO | WO 2013/066362 | 5/2013 |
| WO | WO 2014/146021 | 9/2014 |
| WO | WO2014-162549 | 9/2014 |
| WO | WO 2015/157582 | 10/2015 |
| WO | WO 2016/007186 | 1/2016 |
| WO | WO 2016/007187 | 1/2016 |
| WO | WO 2016/007188 | 1/2016 |

OTHER PUBLICATIONS

Chinese Search report of related Chinese Application No. 201480076629.2 dated Dec. 11, 2018.
Taiwan Search report of related Taiwan Application No. 103143687 dated Sep. 17, 2018.
International Search Report and Written Opinion of related International Application No. PCT/US14/69628 dated Mar. 11, 2015.
International Search report of related International Application No. PCT/US2014/062404 dated Mar. 5, 2015.
International Search Report and Written Opinion of related International Application No. PCT/US2014/062433 dated Mar. 23, 2015.
Mare, Shrirang, et al. "ZEBRA: Zero-Effort Bilateral Recurring Authentication", 2014 IEEE Symposium on Security and Privacy, IEEE, May 18, 2014, pp. 705-720.
Mayrhofer, R., et al., "Shake Well before Use: Intuitive and Securing Pairing of Mobile Devices", IEEE Transactions on Mobile Computing, IEEE Service Center, Los Alamitos, CA, US, vol. 8, No. 6, Jun. 1, 2009, pp. 792-806.
International Search Report and Written Opinion of related International Application No. PCT/US2014/062472 dated Mar. 23, 2015.
International Search Report and Written Opinion of related International Application No. PCT/US2015/025213 dated Jun. 15, 2015.
International Preliminary Report on Patentability of related International Application No. PCT/US14/69628 dated Jul. 21, 2016.
International Preliminary Report on Patentability of related International Application No. PCT/US2015/025213 dated Oct. 20, 2016.
International Preliminary report on Patentability of related International Application No. PCT/US2014/062404 dated Jan. 19, 2017.
International Preliminary Report on Patentability of related International Application No. PCT/US2014/062472 dated Jan. 19, 2017.
International Preliminary Report on Patentability of related International Application No. PCT/US2014/062433 dated Jan. 19, 2017.
International Search Report and Written Opinion of related International Application No. PCT/EP2016/059616 dated Jun. 2, 2016.
International Preliminary Report on Patentability of related International Application No. PCT/EP2016/059616 dated Nov. 9, 2017.
Chinese Search report of related Chinese Application No. 201580031100.3 dated Apr. 10, 2019.
Chinese Search report of related Chinese Application No. 201580031100.3 dated Jul. 19, 2018.
Chinese Search report of related Chinese Application No. 201480076629.2 dated May 31, 2019.
Chinese Office Action of Chinese Application No. 201480076629.2 dated Sep. 9, 2019.
Chinese Office Action of Chinese Application No. 201480080414.8 dated Jul. 24, 2019.
Chinese Search report of Chinese Application No. 201480080414.8 dated Jul. 16, 2019.

* cited by examiner

| TIME | DATE | BG (mg/dL) | LOCATION ID | SPEED (mph) | NOTES |
|---|---|---|---|---|---|
| 4:05PM | 11-Nov | 133 | 45.28107000, -75.71983333 | 0 | At work |
| 1:32PM | 11-Nov | 158 | 45.28157396, -75.71982419 | 2.3 | Walking back from lunch |
| 8:44AM | 11-Nov | 114 | 45.28123547, -75.71977622 | 34.4 | Riding train to work |
| 2:03PM | 12-Nov | 197 | 45.28156562, -75.71977345 | 2.9 | Walking home from movies |
| 11:35AM | 12-Nov | 101 | 45.28107004, -75.71983336 | 0 | Watching TV |

LOCATION-BASED WIRELESS DIABETES MANAGEMENT SYSTEMS, METHODS AND APPARATUS

RELATED APPLICATIONS

The present application claims priority to US Provisional Application No. 62/154,600 filed on Apr. 29, 2015 and entitled "LOCATION-BASED WIRELESS DIABETES MANAGEMENT SYSTEMS, METHODS AND APPARATUS" which is hereby incorporated by reference herein for all purposes.

FIELD

The present invention relates to diabetes management systems and methods, and more specifically to such systems and methods that use wireless devices for location-based diabetes management.

BACKGROUND

Diabetes mellitus is a serious, life-long disorder that is, as yet, incurable. Each year in the U.S. alone, about 2 million people are diagnosed with diabetes, the 7th leading causes of death in the United States. In 2012, 86 million Americans age 20 and older had pre-diabetes; this is up from 79 million in 2010. In 1993, there were approximately eight million diagnosed cases of diabetes mellitus in the United States and the number has grown to about 21 million currently diagnosed cases. In addition, there are at least 8 million undiagnosed cases.

The effects from diabetes on the health care system are startling. In the U.S., the cost of hospitalizations, supplies, lost work, disability payments and premature deaths from diabetes reached more than $245 billion in 2012 alone. In addition, the long-term complications associated with diabetes, particularly when poorly managed, can lead to serious financial and human consequences. Serious diabetes-related complications, including cardiovascular disease, kidney disease, nerve damage, blindness, circulatory problems (which can lead to amputations), stroke, heart disease and pregnancy complications, are estimated to cost more than $176 billion annually. Some health maintenance organizations estimate that while only 3.1% of their covered patients have diabetes, diabetic patients account for over 15% of their total healthcare costs.

Research conducted by the National Institute of Health has shown that if people with diabetes closely monitor and control their blood glucose levels, they will enjoy significant health benefits. Consistent management of diabetes, which includes diet, exercise and aggressive monitoring and control of blood glucose levels, can lessen the risk of serious complications and potentially reduce some diabetes-related conditions by more than half.

The study further revealed that active management of diabetes could, among other benefits, reduce eye disease by up to 76%, reduce kidney disease by up to 50% and reduce nerve disease by up to 60%. Furthermore, treatment regimens necessitate tightly controlled glucose levels, which inherently cause an increased risk of more frequent hypoglycemic episodes. A very real issue facing many diabetics is the fear and possibility of falling into a hypoglycemic coma, or experiencing other diabetic emergencies, without external assistance. Likewise, the fear of a diabetic emergency in a child or other dependent confronts many parents and guardians of diabetic individuals. The possibility of a diabetic emergency hinders both the diabetic individual and the guardian from leading active, independent lifestyles. Thus, what are needed are improved diabetes management systems and methods.

SUMMARY

In some embodiments, a method for diabetes management using location-based reminders is provided. The method includes requesting a user select a diabetes management related task to be reminded to perform; requesting the user select a location at which the user is to be reminded to perform the selected diabetes management related task; monitoring the user's location; detecting the user has entered the selected location; triggering the reminder in response to detecting the user has entered the selected location; and presenting the reminder to the user.

In other embodiments, a method of helping a user locate a blood glucose meter (BGM) is provided. The method includes receiving a request from a user to help locate the user's BGM; identifying a most recent data transfer from the BGM based on a stored date and time associated with the most recent data transfer from the BGM; retrieving a stored location ID associated with the identified most recent data transfer from the BGM; and displaying a map with the retrieved location ID represented as the last known location of the BGM.

In still other embodiments, a method of helping a user improve blood glucose control is provided. The method includes recording a plurality of blood glucose measurements; associating each recorded blood glucose measurement with a location ID; determining location types for each recorded blood glucose measurement based on the associated location ID; identifying patterns of diabetes management events corresponding to particular location types; and offering to set a reminder that will trigger at the location types corresponding to a pattern of a diabetes management event.

Numerous other aspects are provided in accordance with these and other aspects of the invention. Other features and aspects of the present invention will become more fully apparent from the following detailed description, the appended claims and the accompanying drawings.

DESCRIPTION

For the purposes of promoting an understanding of the principles of embodiments of the invention, reference will now be made to the examples illustrated in the drawings and specific language will be used to describe the same. It will nevertheless be understood that no limitation of the scope of the invention is thereby intended, and any alterations and further modifications in the illustrated embodiments, and any further applications of the principles of the invention as illustrated therein as would normally occur to one skilled in the art to which the invention relates are contemplated herein.

Embodiments of the present invention provide systems, apparatus and methods for an improved diabetes management system (DMS) that uses location tracking. Embodiments of the present invention include software applications and systems adapted to provide an enhanced system for managing diabetes adapted to provide location-based reminders, to locate a lost blood glucose meter, and to help a user understand how their lifestyle affects their blood sugar levels. Using a portable, wireless device such as, for example, a smartphone with a global positioning system (GPS) module, embodiments of the present invention include a software application (e.g., a DMS app) operable to receive blood glucose measurements, receive location tracking information (e.g., GPS data), and store the measurements associated with corresponding location tracking information in a DMS database for correlating the measurements with user activities and patterns based on location.

Some embodiments of the present invention enable PWDs to become more active in their diabetes management by enabling receipt of reminders from the DMS App based on their location. In order to manage their disease, people with diabetes often test their blood glucose multiple times per day and keep track of their carbohydrate intake, exercise, and insulin doses. To record these metrics and ensure they keep to their testing regimen, people with diabetes (PWDs) can use diabetes management systems on paper, on a computer, or on their smart devices. Some PWDs may be less active in their management because they are forgetful or unmotivated.

Providing a facility to set location-based reminders to test their blood glucose, take their medication, or perform other diabetes management-related tasks, can help a PWD become more active and involved in their health management.

According to embodiments of the present invention, a user can set a reminder within a DMS App that, when triggered, will prompt a user to test their blood glucose level, take their medication, log their activity, log their carbohydrate intake and/or any other diabetes-related task. Instead of, or in addition to, being triggered at a specific time or date, the reminder can be set to trigger as the user is leaving from or arriving at a pre-defined location, or in some embodiments, at a pre-defined type of location (e.g., based on a pre-defined category such as a restaurant, movie theater, mall, park, arena, gym, etc.). The geographic location point specified by the user is represented as a circle with a configurable radius defined by the system. This enables the system to filter out small movements and to trigger the reminder only in response to significant changes in location.

An example of set a reminder can be in the form of a spoken prompt to the DMS device. For example, the user can say to the DMS App: "Remind me to test my blood sugar when I am arriving at the gym", where "the gym" is a specific location that the user has defined, or in some embodiments, "the gym" can be any gym, exercise place, or fitness center that the system can identify using a pre-defined location ID database such as, for example, a business directory.

Some embodiments of the present invention enable PWDs to locate a lost blood glucose meter (BGM) via the DMS App. Blood glucose meters can be relatively small and therefore, easy to misplace. In some embodiments, when the BGM readings are synced (e.g., uploaded from the BGM to the DMS device) via a wireless communication protocol (e.g., such as Bluetooth) using the DMS App, the DMS App can record the user's current location. If the user later wants help finding the BGM, the recorded location can be recalled and shown on a map so that the user knows the last location their BGM was "seen" by the DMS App.

In some embodiments, the DMS App can attempt to detect the BGM by trying to communicate with the BGM. If successful (e.g., the BGM is in range and can be remotely activated via, for example, a wake function implemented on the BGM), the DMS App can provide further location information based on signal strength detected from the activated BGM. Alternatively, the BGM can be activated and signaled to trigger an audible alarm to help find the BGM.

Some embodiments of the present invention enable PWDs to learn more about how their lifestyle affects their blood glucose levels. PWDs may not realize what factors are affecting their glucose levels, and their activities, behaviors or tendencies at particular locations or types of locations may be such a factor. For example, PWDs eating or exercise behaviors may change when they are on vacation, in a different city, or at someone else's house. Tagging or associating blood glucose readings with the locations at which the readings were made can allow the DMS App to detect patterns in how the user's behavior as indicated by location is affecting their blood glucose levels. In other words, using a pattern recognition engine, the DMS App can identify, for example, high glucose levels associated with particular locations. Using the location ID database, the DMS App can correlate poor glucose control instances with going to the type of locations, e.g., such as visiting a mall, where there may be many high glycemic food temptations (e.g., ice cream, cookies, cinnamon buns, doughnuts, etc.).

Likewise, using the pattern recognition engine, the DMS App can identify, for example, maintaining good control over glucose levels associated with particular locations. Using the location ID database, the DMS App can correlate good glucose control periods with going to the type of locations, e.g., such as visiting a gym or a health food store, where there may be opportunities or options that make it easier to maintain good glycemic control (e.g., exercise, salad bar, etc.). In another example, the DMS App might recognize that on days the user goes to the office cafeteria during lunchtime or goes for a walk in a park after lunchtime, the user experiences good glycemic control. The DMS App can display or present praise/commendations to the user for the good glucose control and/or make a suggestion on a future day as lunchtime approaches to consider eating at the cafeteria and taking a walk in the park afterward. The DMS App can even suggest a different park for variety. For example, by associating more than one location with the location type "park", the DMS App can come up with new ideas for the user.

In another example, if a blood glucose reading is received in the DMS device from the BGM within, e.g., five minutes of a time stamp recorded using a location tracking module (e.g., a GPS module) in the DMS device, the system can assume that the BGM and DMS device were at the same location at the time the reading was taken and associate the reading with the location information in a DMS database in the DMS device. In other words, the DMS device can record the current location and keep a log of these "location-tagged" readings. In some embodiments, the DMS App can allow the user to review the location tags assigned to the readings and add to or correct them. An integrated pattern recognition engine in the DMS App which finds patterns in glucose levels, testing frequency, and locations can be used to detect hidden correlations between the data elements which reveal location based activities that are helpful or hurtful to successful diabetes management. For example, if a person has been frequently "testing high" (e.g., experiencing BGM readings indicating a high blood glucose level) at a certain location, the system can notify the user that their blood glucose has been running high at this location, and suggest methods of correcting or altering this pattern.

In some embodiments, the DMS App can identify time periods during which it would be helpful to have a reading taken and the location of the reading identified. For example, if the DMS App notices a pattern where the user is recovering from a high glucose level every other afternoon at 4 PM but there is nothing in the data to suggest why that pattern exists (e.g., the user is at his office), the DMS App can ask the user to take a reading at, for example, 3 PM every other day to see if the user goes to a location that might correlate with poor glucose control such as, for example, an ice cream parlor.

Additionally, in embodiments where the DMS device includes or has access to a location ID database that allows the DMS App to identify the locations (e.g., a business phone directory, a white pages directory, Yelp, Foursquare, GoogleMaps, etc.), the system can identify the type of location (e.g., workplace, coffee shop, cinema, gas station, etc.). In another example, assume the location type for three BGM readings is identified as movie theatres. If the system detects three high glucose readings near that type of location each time the user went to the movies. The DMS App can use the pattern recognition engine to recognize the pattern, inform the user of the pattern, and suggest that the user choose lower-carbohydrate snacks when going to the movies. Alternatively or additionally, the DMS App can ask if the user would like to set a reminder (e.g., "Eat fewer carbohydrates!") to trigger when arriving at this type of location.

In some embodiments, the location tagging function implemented in the DMS App can prompt the user to label certain locations that maybe unclear instead of using a business directory to guess the location ID based on the coordinates. For example, the DMS App can use the business directory to make a best guess (e.g., when the location coordinate information is unclear because it indicates more than one possibility) and have the user confirm, for example asking "Are you at Dunkin Donuts?" If the user responds indicating "No", the DMS can present a list of other locations in the general area from which to choose and/or ask the user to add a new location name and/or location type. In this manner, the DMS App can building a customized database of locations that becomes more accurate as the user logs more location-tagged readings. Thus, if there are multiple locations that are very close to one another, the DMS App can make a more educated guess at where the user actually is at any given time. For example, where a burrito shop and a sandwich shop are next to each other, and the user has previously tagged one of their readings as being taken at the burrito shop, the next time the user is taking their blood sugar at that location, the DMS App would first suggest the burrito shop is the current location.

Figure 1:
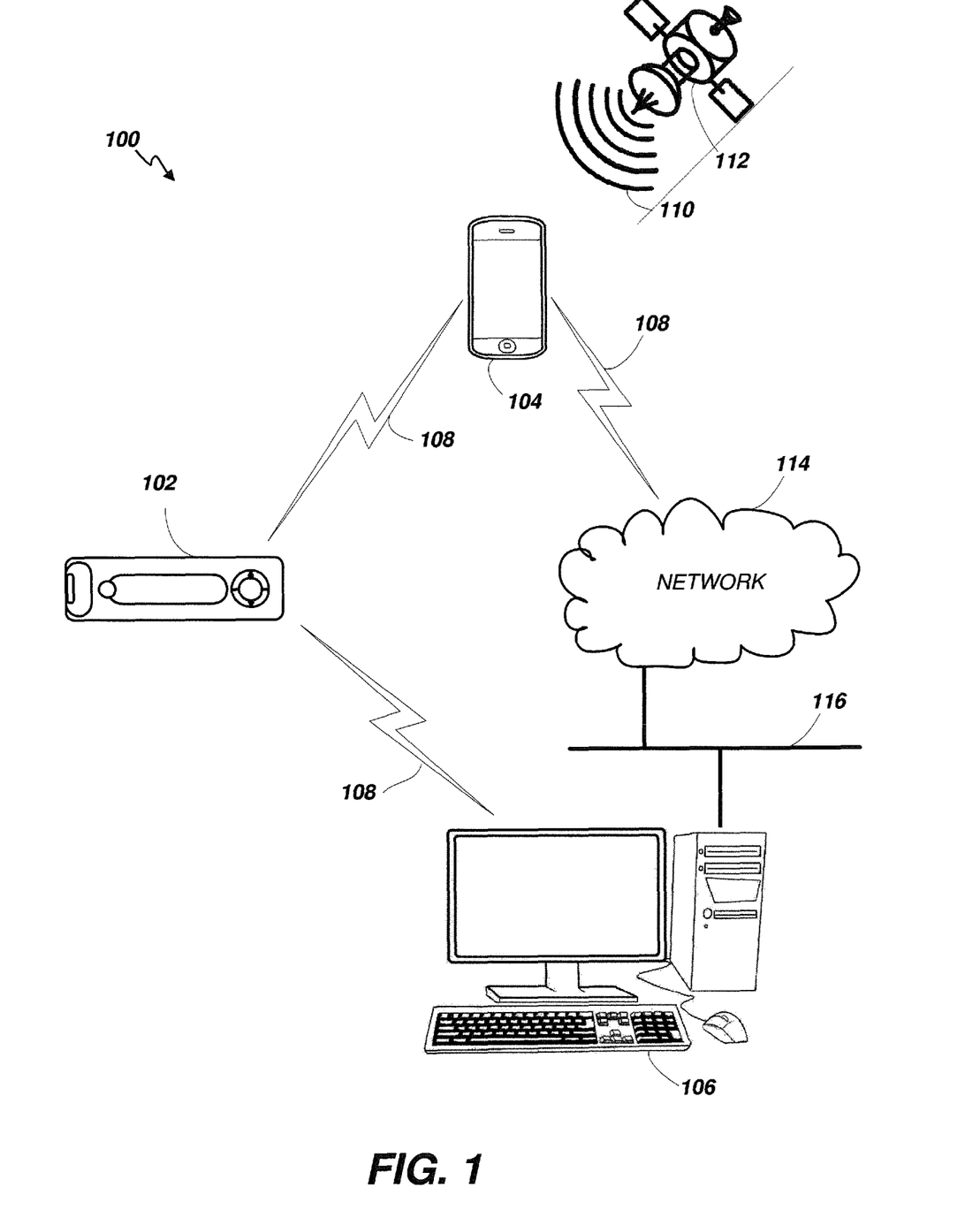
FIG. 1 is a schematic block diagram depicting an example system according to embodiments of the present invention.

Turning now to FIG. 1, an example of a DMS 100 is depicted. The DMS 100 includes a BGM 102 that is adapted to couple to a DMS device 104 (e.g., a smart phone, tablet, smart watch, etc. operative to execute a DMS App) and/or a computer 106 operative to run a DMS program. The BGM 102 and the DMS device 104 are operated by a user (e.g., a PWD) using the DMS 100 to help improve their management of their diabetes. The DMS device 104 and the computer 106 can be coupled to the BGM 102 wirelessly (e.g., via a wireless signal protocol 108 such as Bluetooth) or via a wired connection (e.g., via a universal serial bus (USB) connection).

In some embodiments, the DMS device 104 is adapted to receive GPS signals 110 from one or more satellites 112 for location tracking. In some embodiments, a health care provider (HCP) or user can operate the computer 106 to receive glucose readings data from the BGM 102 and location data from the DMS device 104 via a network 114 (e.g., the Internet). In some embodiments, the computer 106 can receive glucose readings data directly from the BGM 102 via a wired, wireless, or and any other practicable means (e.g., a memory card exchange). The computer 106 can couple to the network 114 via a wired connection (e.g., via Ethernet 116) or via any other practicable means. Likewise, the DMS device 104 can couple to the network 114 via a wireless signal protocol 108 (e.g., Wi-Fi) or via any other practicable means.

Figure 2:
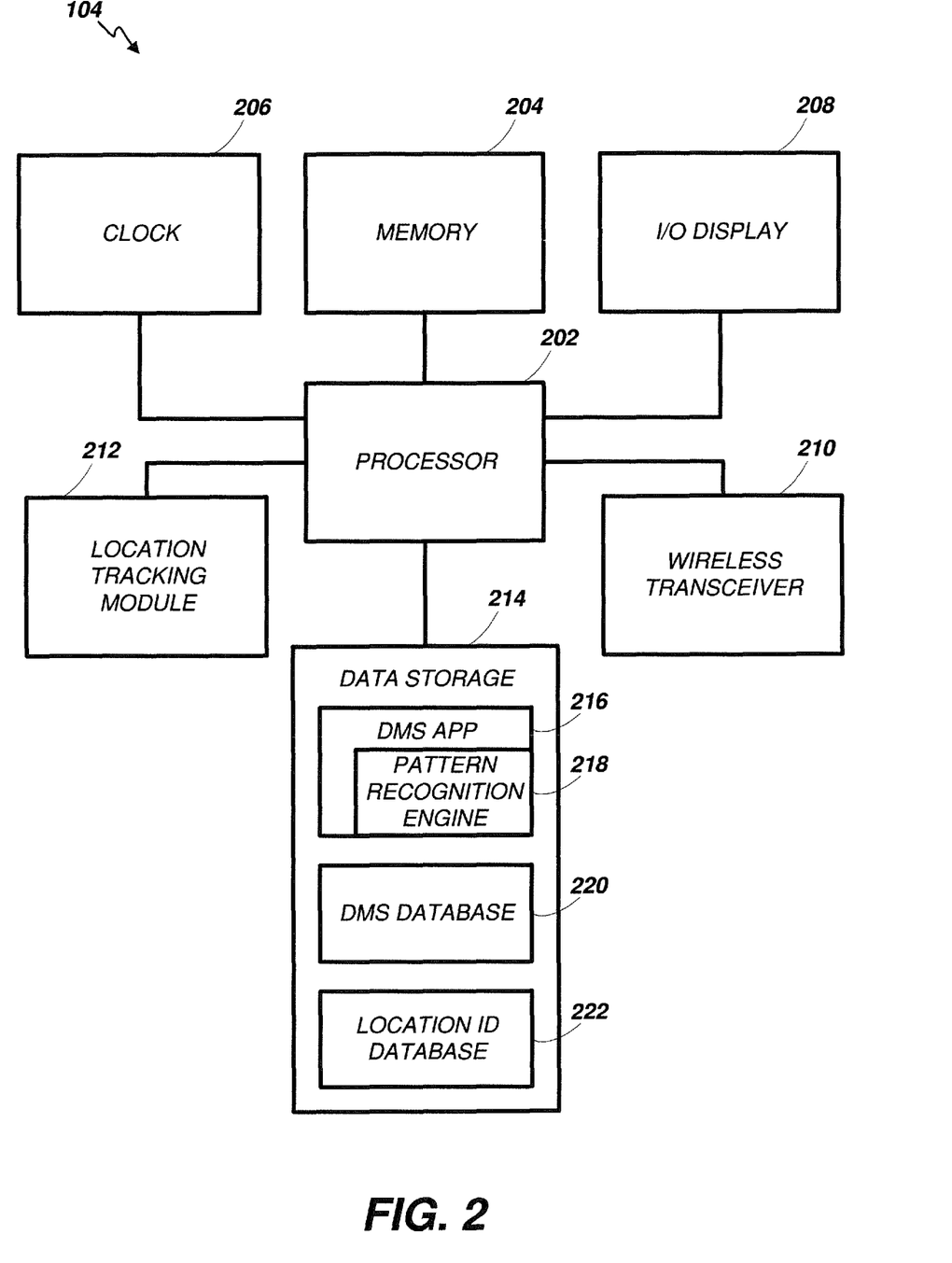
FIG. 2 is a schematic block diagram depicting an example apparatus according to embodiments of the present invention.

Turning now to FIG. 2, details of an example DMS device 104 are depicted. Note that in some embodiments, the DMS device 104 can be implemented on a computer 106 and the computer 106 can be a portable, wireless device (e.g., a laptop, tablet PC, etc.). A DMS device 104 can include a processor 202 coupled to a memory 204 for storing instructions executable on the processor 202. The processor 202 can be coupled to a clock 206 (e.g., a clock generator module, an oscillator, etc.) for generating date and time-stamp data to associate with BGM data and/or location data.

The processor 202 can be coupled to an input/output (I/O) display 208 that can include any number of input devices (e.g., such as a touch screen, "soft" programmable buttons/keys, hardware buttons and switches, keyboard, optical and magnetic readers/scanners, cameras, sensors, transducers, accelerometer, microphones, audio input, USB and LAN ports, and the like) and any number of output devices (e.g., such a display, an audio speaker, haptic devices, a vibrator, light emitting diodes (LEDs), a printer, audio output, USB and LAN ports, and the like). The I/O display 208 can be used to communicate with the user to set reminders and to present reminders as well as for conventional I/O functions.

The processor 202 can be coupled to a wireless transceiver 210 that can include cellular communications facilities and two-way radio signal communication facilities such as Wi-Fi, Bluetooth, and other communications modules. In other words, the wireless transceiver 210 can include any type of device and/or software that is able to communicate across the network 114. For instance, the wireless transceiver 210 can include a cellular communication type device, a Wi-Fi type device, and/or an infrared port, to name just a few.

The processor 202 can be coupled to a location tracking module 212 which can, for example, include any type of system for location determination that can be hardware and/or software based. For example, the location tracking module 212 can include a global positioning system (GPS), an assisted GPS-type system, a compass, and/or an accelerometer, as well as other components for detecting the position or location of the DMS device 104. In some embodiments, the DMS device 104 can directly locate itself without receiving GPS signals. In such embodiments, the DMS device 104 triangulates the location of the DMS device 104 based on internet protocol (IP) addresses of one or more routers with known locations through which the DMS device 104 communicates. In another example, the location of the DMS device 104 can be determined based on the known location of a Wi-Fi hotspot through which the DMS device 104 communicates. Combinations of techniques can be also used for location detection. For instance, the DMS device 104 can be located based on some combination of Wi-Fi router location data, 3G/4G cellular tower location data, and GPS coordinate data. The DMS 100 also allows the user to manually enter their location, such as when GPS line of sight is not available.

The processor 202 can be coupled to a data storage device 214 such as non-volatile memory that allows persistent storage of data structures, data, and instructions that can be loaded into the memory 204 for use/execution by the processor 202. The data storage device 214 can be implemented using one or more solid state drives, hard drives, memory cards, or the like. The data storage device 214 includes a data structure that can include a DMS App 216 (that in some embodiments includes an integrated pattern recognition engine 218), a DMS database 220, and a location ID database 222.

The DMS App 216 implements the methods and processes described herein. The pattern recognition engine 218 is used by the DMS App 216 to implement detection of location-based behaviors that result in helpful or hurtful events (e.g., good or poor blood glucose control). An example of a pattern recognition system is disclosed in U.S. Pat. No. 8,758,245 to Ray et al. which is incorporated herein for all purposes. An example of a DMS database 220 is described below with respect to FIG. 3.

The location ID database 222 can be embodied as a table listing locations or location types such as commercial establishments, private homes, geographic landmarks, shopping centers, government buildings, public venues, parks, recreation facilities, etc. wherein each listing is associated with a location identifier such as GPS coordinates, longitude and latitude coordinates, positioning data relative to known landmarks, etc. In some embodiments, the DMS App 216 is operable to identify the location or location type using GPS coordinates as an index into the location ID database 222. In other words, the DMS App 216 can use the location ID database 222 to convert/translate GPS coordinates to the name of a location or the type of establishment/location (e.g., cinema, home, restaurant, mall, etc.) In some embodiments, the locations can each be associated with a location type. For example, Joe's Diner, MacDonald's®, Pizza Hut®, Outback®, and Olive Garden® can all be associated with a location type called Restaurant.

Figure 3:
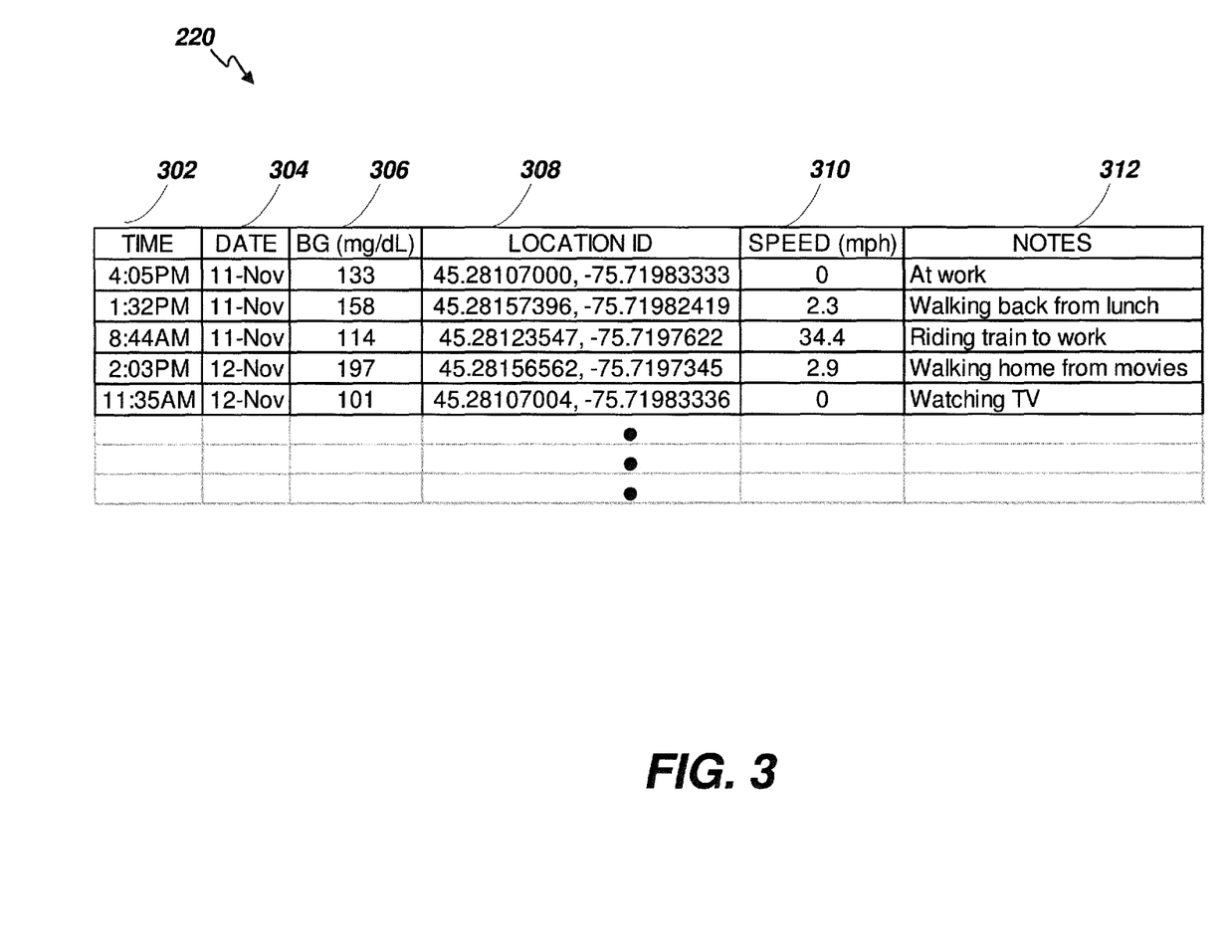
FIG. 3 is a tabular representation of an example database according to embodiments of the present invention.

Turning now to FIG. 3, an example of a DMS database 220 is depicted in tabular form. Note that the format of the particular example depicted is merely illustrative of one possibility. Many alternative data arrangements and database types could be used. Any format or database type practicable to implement the data structure and relationships depicted could be used. Note also that only a limited number of entries are shown in the example and that in an actual implementation, there may be many more entries (e.g., thousands of rows).

Each entry in the DMS database 220 shown can include a time field 302, a date field 304, a blood glucose level field 306, a location ID field 308, a speed field 310, and a notes field 312. The time field 302 is adapted to store data representative of a timestamp that indicates the time a blood glucose reading associated with the entry occurred. The date field 304 is adapted to store data representative of a datestamp that indicates the date the blood glucose reading associated with the entry occurred.

The blood glucose level field 306 is adapted to store data representative of a blood glucose level of the blood glucose reading associated with the entry. The location ID field 308 is adapted to store data representative of an approximate location (e.g., in GPS coordinates) of the DMS device 104 when the blood glucose reading associated with the entry occurred. The speed field 310 is adapted to store data representative of a speed at which the DMS device 104 was being moved when the blood glucose reading associated with the entry occurred. The notes field 312 is adapted to store data representative of information provided by the user and associated with the entry.

In some embodiments, many additional fields can be included in the DMS database 220. For example, a medication dosage field, a food intake field, a carbohydrates consumed field, an exercise performed field, and the like can be included. In some embodiments, one or more fields to store the location name and/or location type can also be included. In some embodiments, the DMS App 216 can associate the location ID data with the appropriate blood glucose reading entry in the DMS database 220 based upon timestamp data. Likewise, the DMS App 216 can associate the location name or type with the appropriate blood glucose reading entry in the DMS database 220 based upon the location ID data using the location ID database 222.

In some embodiments, the DMS App 216 can use the data in the speed field 310 along with the location ID data and the information in the notes field 312 to search for patterns that indicate the user is engaging in a particular activity. For example, if the speed field 310 for an entry indicates the user is moving at a typical jogging pace, the location ID field 308 indicates the user is at a public park, and the notes field 312 indicates the user is "exercising," the DMS App 216 can conclude that the user is jogging. The DMS App 216 can store this determination and use it in future pattern recognition processing to trigger providing advice or a reminder based on the DMS detecting the user engaging in the particular activity (as opposed to merely being at a particular location or type of location).

Figure 4:
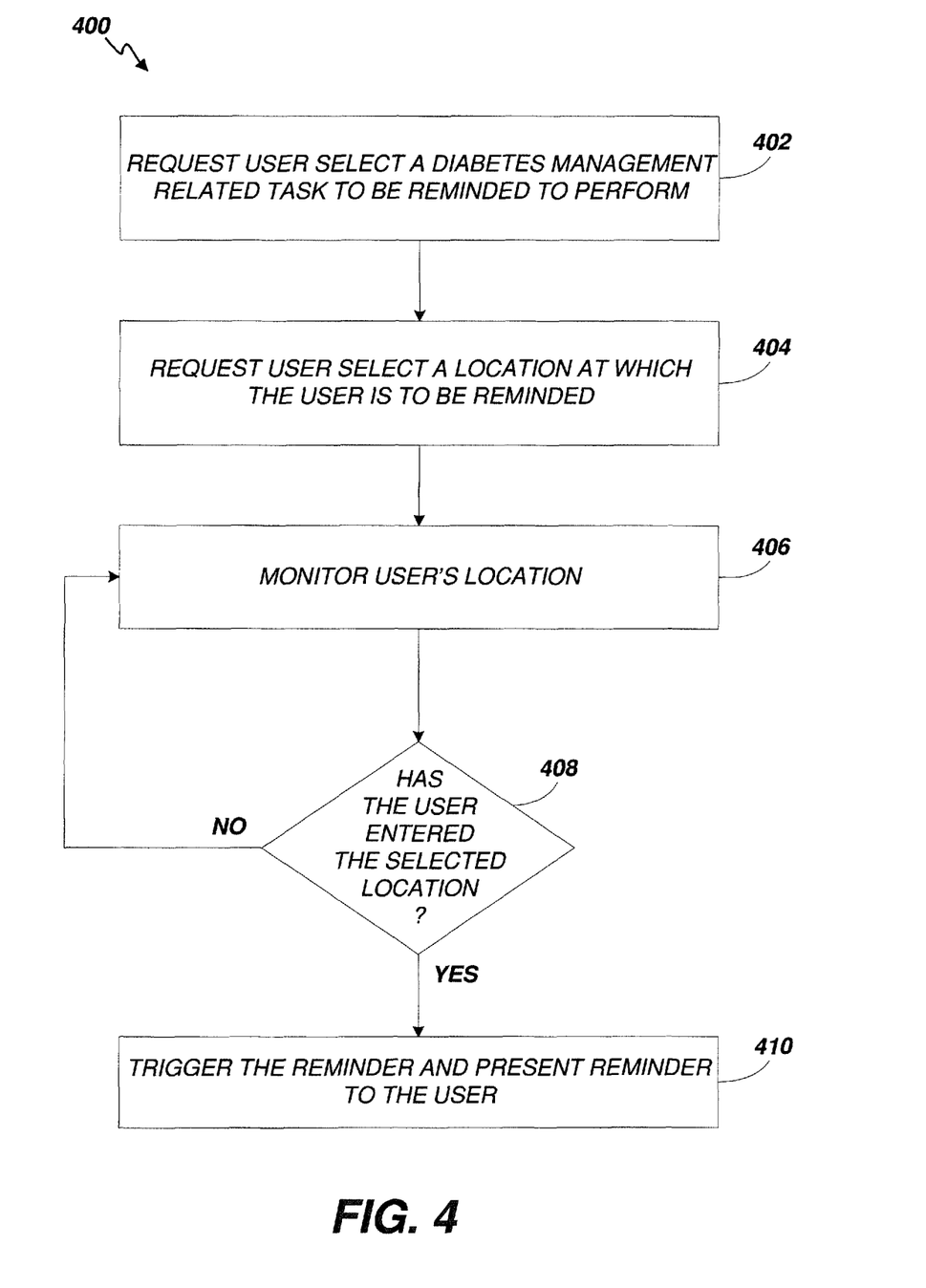
FIG. 4 is a flowchart depicting a first example method according to embodiments of the present invention.

Turning now to FIG. 4, an example of a method 400 of setting and triggering location-based reminders for diabetes management is depicted in a flowchart. The DMS App running on the DMS device requests the user to select a diabetes management related task (e.g., test blood glucose level, take medication, log activity or carbohydrate consumption, etc.) that the user would like to be reminded to perform (402). The DMS App then asks the user to identify a location (or type of location) at which the user is to be reminded to perform the diabetes management related task (404). The DMS monitors the user's location (406) and checks to see if the user has entered a perimeter around the selected location (408). If not, flow returns to monitoring the user's location (406). If yes, the reminder is triggered and the DMS App presents the reminder to the user (410).

Figure 5:
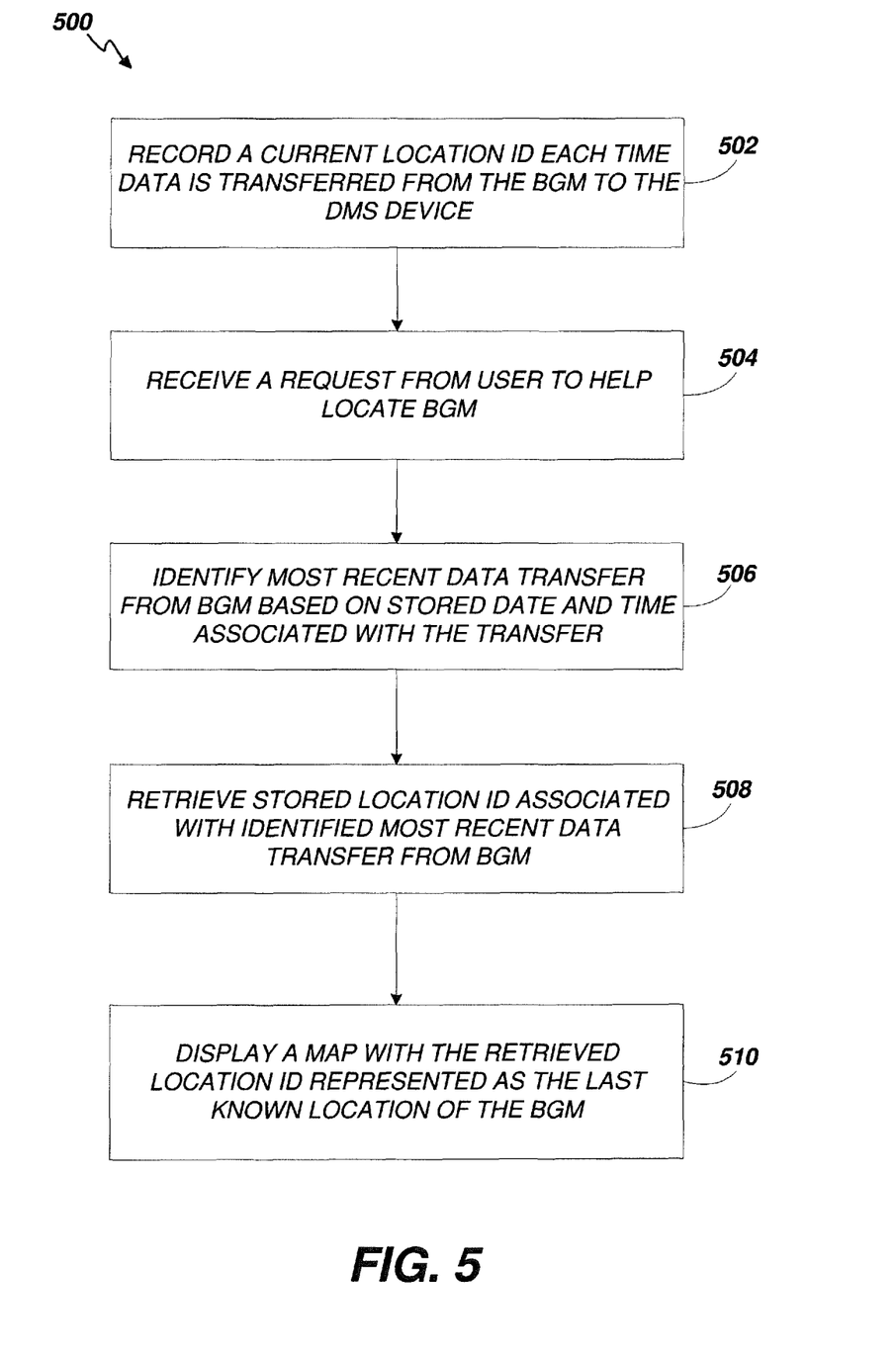
FIG. 5 is a flowchart depicting a second example method according to embodiments of the present invention.

FIG. 5 is a flowchart depicting an example method 500 of helping a user to locate a BGM using the DMS App. Initially, the DMS App stores the current location ID each time data is transferred (e.g., each time a blood glucose reading is taken) from the BGM to the DMS device (502). Next, at some point in the future, the DMS App receives input from the user requesting help locating the user's BGM (504). In response, the DMS App identifies the most recent data transfer from the BGM based on a stored time and date associated with the transfer (506). The DMS App then retrieves stored location ID associated with the identified most recent transfer (508). Finally, the DMS App displays a map with the retrieved location ID represented as the last known location of the user's BGM (510).

Figure 6:
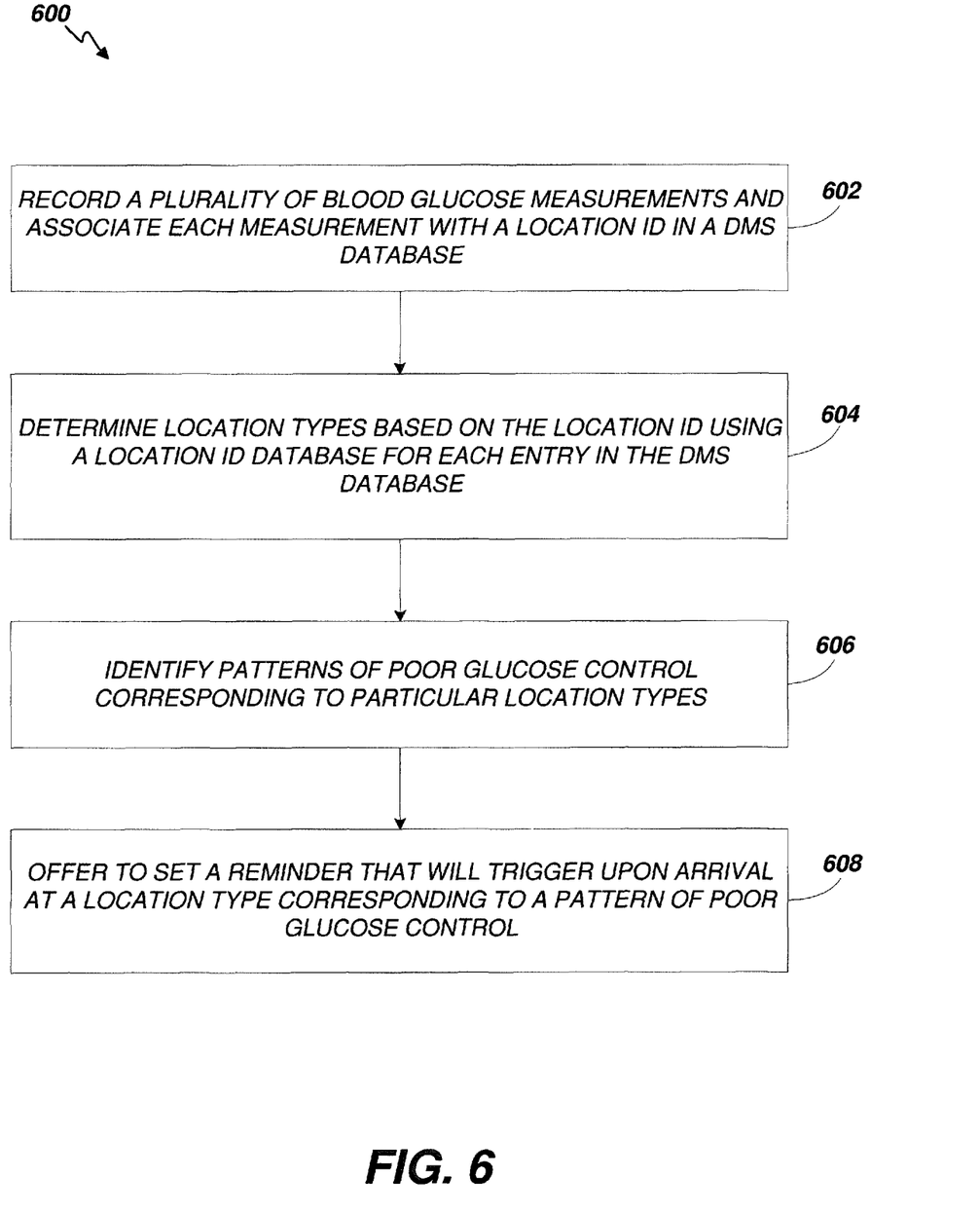
FIG. 6 is a flowchart depicting a third example method according to embodiments of the present invention.

FIG. 6 is a flowchart depicting an example method 600 of helping a user improve blood glucose control using pattern recognition to suggest location-based reminders. A plurality of blood glucose measurements collected over a period of time are each associated with a location ID in a DMS database (602). A location ID database is used to determine location types based on the location ID for each entry in the DMS database (604). Patterns of poor glucose control are identified which correspond to particular location types (606). The DMS App then offers to set a reminder that will trigger upon arrival at a location type corresponding to a pattern of poor glucose control (608).

Figure 7:
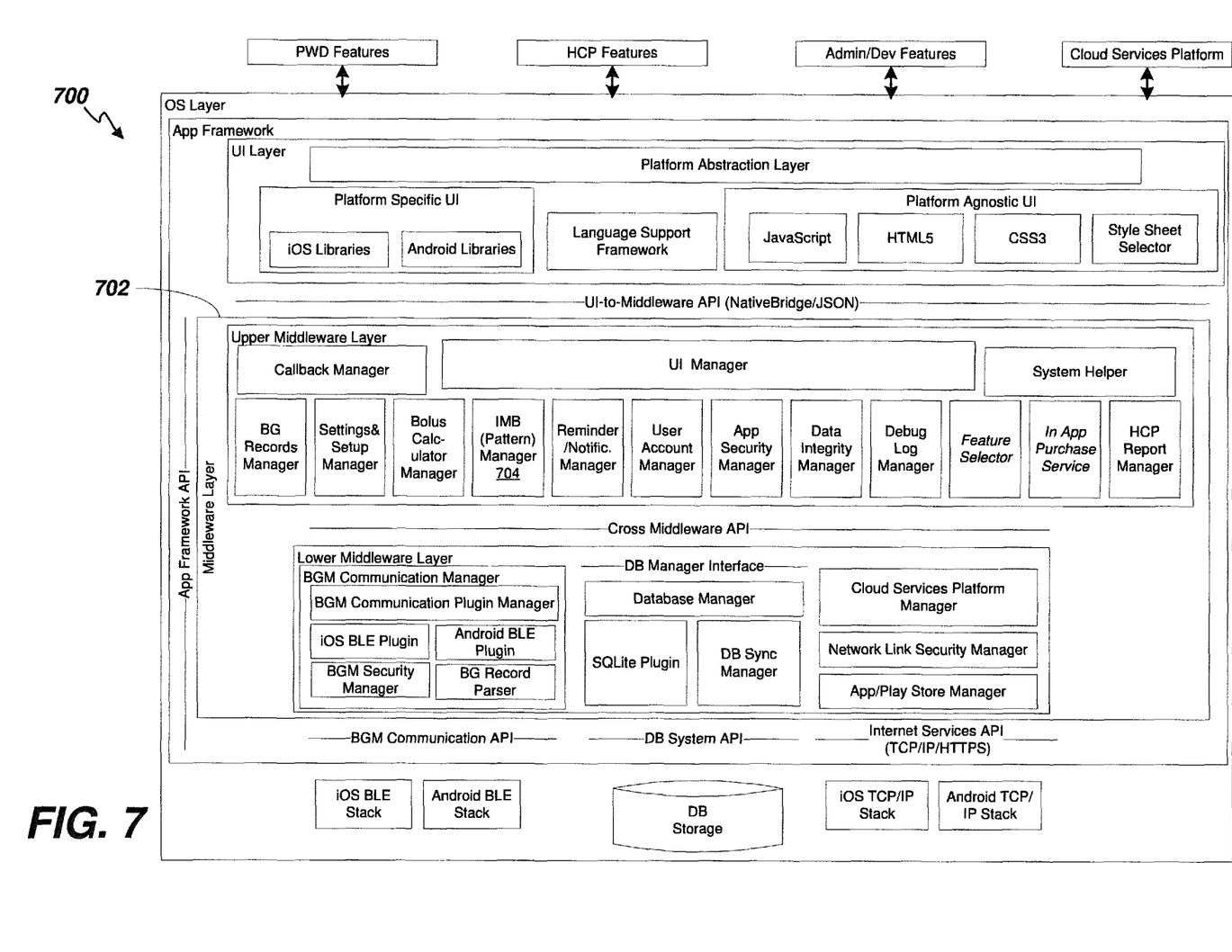
FIG. 7 is a block diagram illustrating an example structure of a system software architecture according to embodiments of the present invention.
Figure 8:
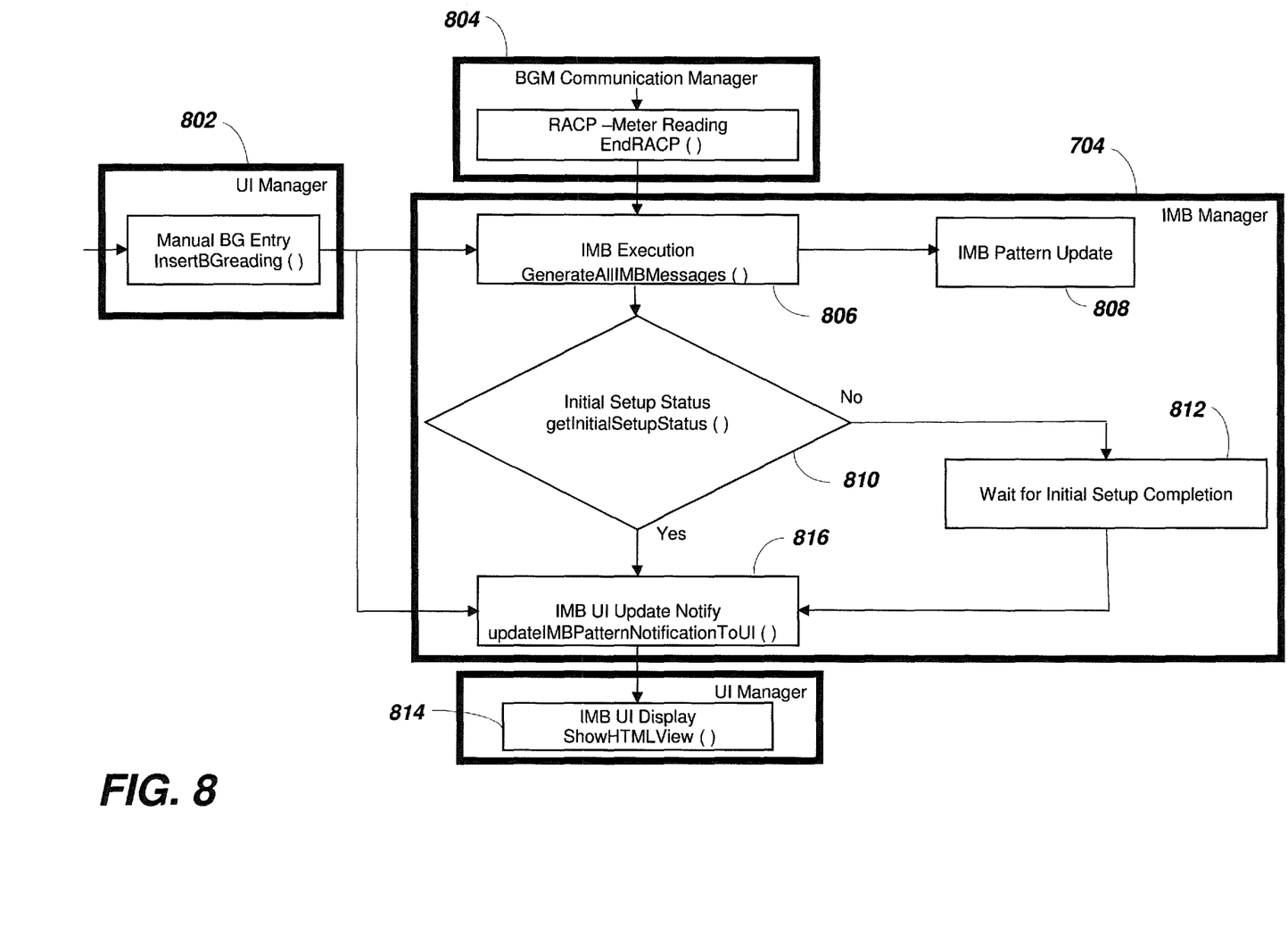
FIG. 8 is a flowchart depicting an example method for an Information and Motivational Behavior (IMB) module according to embodiments of the present invention.

In alternative embodiments, a DMS application can be implemented as part of an integrated system architecture 700 as illustrated in FIG. 7. Residing within the middleware application program interface 702, an Information and Motivational Behavior (IMB) manger 704 can implement the functionality described above. As shown in the flowchart 800 of FIG. 8, the IMB manger 704 can receive BG information either manually through the user interface manager 802 or via the BGM communication manger 804 (e.g., wirelessly). IMB Execution commences with the generation of IMB (e.g., reminder) messages (806) and updates to the stored IMB patterns (808). Based on the initial setup status (810) the IBM manger either waits for setup completion (812) or sends an update notification to the IMB user interface display 814 of the user interface manager 802 (816).

Figure 9:
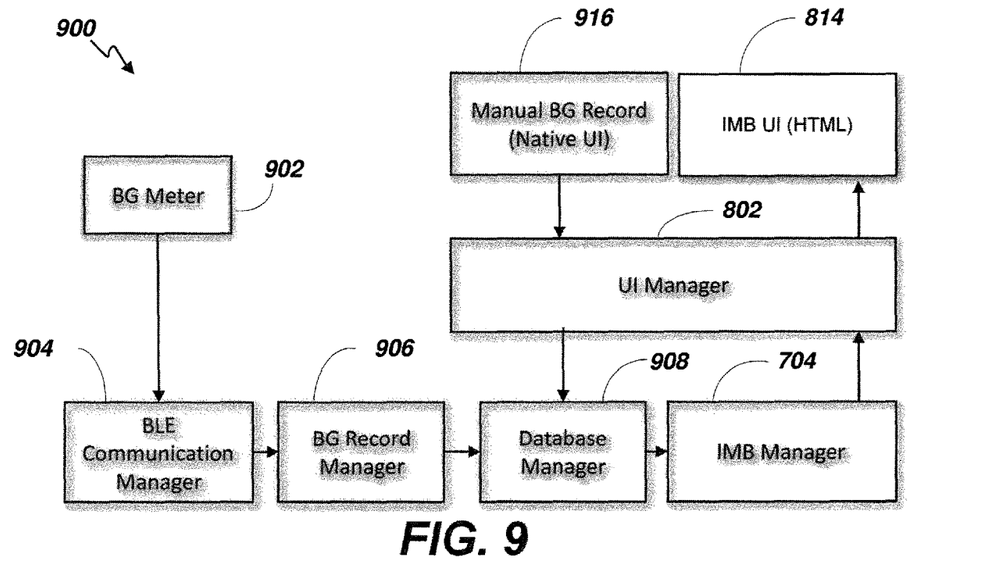
FIG. 9 is a block diagram depicting an example workflow according to embodiments of the present invention.

FIG. 9 is a block diagram that depicts the IMB workflow 900. The BG meter 902 can provide a BG reading to the communication manger 904 (e.g., via Bluetooth Low Energy (BLE) protocol) within the application when the BG meter 902 is connected. The BG Record Manager 906 module will identify the BLE data (e.g., whether incoming data identifies BG reading, a meal marker, or setting data), parse and reform the data as a corresponding record (e.g., a BG/Meal Marker record, etc.) and send it to database manager 908 to be stored in the database. The database manager 908 will store the all BG/Meal Marker/Device Setting data into the database (e.g., an SQLite database) and will perform data read operations from the database. IMB manager 704 executes the IMB module whenever a new BG reading arrives and IMB data will be stored in the database through the IMB pattern Manager and an IMB notification will be sent to IMB user interface 802 for display. The user interface Manager 802 is a gateway for the middleware 702 since all user interface operations (e.g., data reads/writes) to the middleware 702 happen through this module. In some embodiments, IMB notifications will be sent to the HTML level though this module in JSON format. This module gets data from the database, formats the data (e.g., in JSON), and sends the formatted data to the user interface. The Manual BG Records module 916 can also generate BG data records (e.g., from a BG data storage application) that are similar to BG meter records but instead of a BG meter determining BG readings from strip measurements, the data records are "generated" from the application. In the case of manual entry, the Manual BG Records module 916 directly interacts with the database Manager 908 (e.g., to store the manual entry in the database) through user interface Manager 802.

Figure 10:
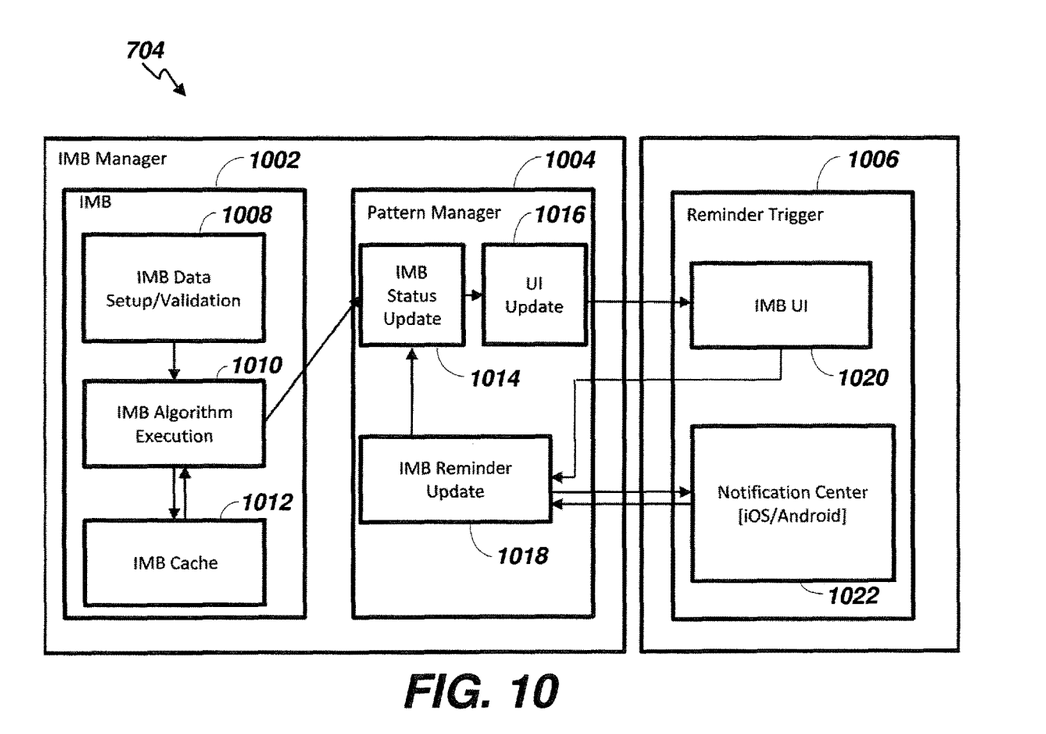
FIG. 10 is block diagram illustrating details of an example Information and Motivational Behavior (IMB) module portion of a system software architecture according to embodiments of the present invention.

FIG. 10 depicts in more detail the structure and components of the IMB manager 704. In some embodiments, the IMB manger 704 includes an IMB module 1002 and a pattern manager module 1004. The IMB manger 704 also interacts with the reminder trigger module 1006.

The IMB Module 1002 includes three sub-modules: the IMB Setup/Validation sub-module 1008, the IMB Algorithm Execution sub-module 1010, and the IMB Cache sub-module 1012. The IMB Data Setup/Validation sub-module 1008 is employed whenever a new BG reading is received, regardless of originating from the BG meter or from manual entry. The IMB module 1002 will enter setup mode, validate the data, and make the decision whether the IMB algorithm should be executed or not. Setup or validation is done via first getting target range values, next resetting the IMB cache 1012, checking the IMB Execution eligibility status based on the current/last executed BG timestamp, and then checking and updating the pattern "timed out" status for already detected IMB pattern in Pattern Manager Module. The IMB Algorithm Execution sub-module 1010 is responsible for execution of the IMB algorithm; updating of the IMB cache 1012 for UI notification; and updating/inserting new detected patterns into the Pattern Manager. The IMB Cache sub-module 1012 functions as a local buffer and holds information about the IMB pattern currently being detected. The information can include the IMB ID and whether the pattern is a delayed pattern or not.

The Pattern manager Module 1004 includes three sub-modules: the IMB Status Update sub-module 1014, UI Update sub-module 1016, and the IMB Reminder Update sub-module 1018. IMB status is an important property of an IMB pattern. The Pattern Manager 1004 updates the IMB pattern status. The IMB Status Update module 1014 can include several pieces of status information. For example, the information can include New Pattern detected information, a Pattern category update (e.g., Active/Archive), a Pattern state update (e.g., Read/Unread), and a Pattern status update (e.g., New/Improved/Invalid/Timeout). The UI Update module 1016 is responsible for presenting detected IMB patterns in the UI. If a reminder has been created during IMB pattern flow, then the IMB Reminder Update sub-module 1018 performs an update of the Reminder ID for the corresponding IMB pattern and an update of the NB reminder triggered status. The Reminder Trigger sub-module 1006 represents a UI 1020 or native 1022 (e,g., Android or IOS) notification center which initiates the creation of a reminder, triggers a reminder, and updates a reminder's status.

Numerous embodiments are described in this disclosure, and are presented for illustrative purposes only. The described embodiments are not, and are not intended to be, limiting in any sense. The presently disclosed inventions are widely applicable to numerous embodiments, as is readily apparent from the disclosure. One of ordinary skill in the art will recognize that the disclosed inventions may be practiced with various modifications and alterations, such as structural, logical, software, and electrical modifications. Although particular features of the disclosed inventions may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

The Title (set forth at the beginning of the first page of this disclosure) is not to be taken as limiting in any way as the scope of the disclosed inventions.

The term "product" means any machine, manufacture and/or composition of matter as contemplated by 35 U.S.C. § 101, unless expressly specified otherwise.

Each process (whether called a method, class behavior, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, component, structure, or article is described herein, more than one device, component, structure or article (whether or not they cooperate) may alternatively be used in place of the single device, component or article that is described. Accordingly, the functionality that is described as being possessed by a device may alternatively be possessed by more than one device, component or article (whether or not they cooperate).

Similarly, where more than one device, component, structure, or article is described herein (whether or not they cooperate), a single device, component, structure, or article may alternatively be used in place of the more than one device, component, structure, or article that is described. For example, a plurality of computer-based devices may be substituted with a single computer-based device. Accordingly, the various functionality that is described as being possessed by more than one device, component, structure, or article may alternatively be possessed by a single device, component, structure, or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, Digital Light Processing (DLP), rear projection, front projection, or the like may be used to form the display.

The present disclosure may refer to a "control system", application, or program. A control system, application, or program, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, Central Processing Unit (CPU) devices, computing devices, microcontrollers, digital signal processors, or like devices. Exemplary processors are the INTEL PENTIUM or AMD ATHLON processors.

The term "computer-readable medium" refers to any statutory medium that participates in providing data (e.g., instructions) that may be read by a computer, a processor or a like device. Such a medium may take many forms, including but not limited to non-volatile media, volatile media, and specific statutory types of transmission media. Non-volatile media include, for example, optical or magnetic disks and other persistent memory. Volatile media include DRAM, which typically constitutes the main memory. Statutory types of transmission media include coaxial cables, copper wire and fiber optics, including the wires that comprise a system bus coupled to the processor. Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read. The terms "computer-readable memory" and/or "tangible media" specifically exclude signals, waves, and wave forms or other intangible or non-transitory media that may nevertheless be readable by a computer.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present invention.

Where databases and/or data structures are described, it will be understood by one of ordinary skill in the art that (i) alternative database structures to those described may be readily employed, and (ii) other memory structures besides databases may be readily employed. Any illustrations or descriptions of any sample databases/data structure presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" generally refers to an information or computing network that can be used to provide an environment wherein one or more computing devices may communicate with one another. Such devices may communicate directly or indirectly, via a wired or wireless medium such as the Internet, LAN, WAN or Ethernet (or IEEE 802.3), Token Ring, or via any appropriate communications means or combination of communications means. Exemplary protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cable TV, satellite links, and the like. Where appropriate encryption or other security measures such as logins and passwords may be provided to protect proprietary or confidential information.

Communication among computers and devices may be encrypted to insure privacy and prevent fraud in any of a variety of ways well known in the art. Appropriate cryptographic protocols for bolstering system security are described in Schneier, APPLIED CRYPTOGRAPHY, PRO- TOCOLS, ALGORITHMS, AND SOURCE CODE IN C, John Wiley & Sons, Inc. 2d ed., 1996, which is incorporated by reference in its entirety.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

The foregoing description discloses only exemplary embodiments of the invention. Modifications of the above disclosed apparatus and methods which fall within the scope of the invention will be readily apparent to those of ordinary skill in the art. For example, although the examples discussed above are illustrated for an electricity market, embodiments of the invention can be implemented for other markets.

Accordingly, while the present invention has been disclosed in connection with exemplary embodiments thereof, it should be understood that other embodiments may fall within the spirit and scope of the invention, as defined by the following claims.

What is claimed is:

1. A method of diabetes management based on location-based reminders, the method comprising:
    requesting a user select a diabetes management related task to be reminded to perform;
    requesting a user select a location at which the user is to be reminded to perform the selected diabetes management related task;
    monitoring the user's location;
    detecting the user has entered the selected location;
    triggering the reminder in response to detecting the user has entered the selected location; and
    presenting the reminder to the user.

2. The method of claim 1 wherein requesting a user select a diabetes management related task includes requesting a user select at least one of being reminded to test a blood glucose level of the user, being reminded to take medication, being reminded to log activity, and being reminded to log carbohydrate consumption.

3. The method of claim 1 wherein requesting the user select a location includes determining a perimeter around the selected location.

4. The method of claim 3 wherein detecting the user has entered the selected location includes determining that the user has entered the perimeter.

5. The method of claim 1 wherein requesting the user select a location includes requesting the user select a type of location.

6. The method of claim 5 wherein triggering the reminder includes triggering the reminder in response to detecting the user has entered the selected type of location.

7. The method of claim 1 further including detecting the user has departed the selected location; and triggering the reminder in response to detecting the user has departed the selected location.

* * * * *